(12) United States Patent
Scavone et al.

(10) Patent No.: US 8,147,808 B2
(45) Date of Patent: *Apr. 3, 2012

(54) CONSUMER NOTICEABLE IMPROVEMENT IN WETNESS PROTECTION USING SOLID ANTIPERSPIRANT COMPOSITIONS

(75) Inventors: Timothy Alan Scavone, Loveland, OH (US); George Endel Deckner, Cincinnati, OH (US); Zerlina Guzdar Dubois, Mason, OH (US); Theresa Louise Johnson, South Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/712,616

(22) Filed: Mar. 1, 2007

(65) Prior Publication Data

US 2007/0248552 A1 Oct. 25, 2007

Related U.S. Application Data

(63) Continuation-in-part of application No. 11/418,607, filed on May 5, 2006, which is a continuation-in-part of application No. 11/132,824, filed on May 19, 2005.

(51) Int. Cl.
| | |
|---|---|
| A61Q 15/00 | (2006.01) |
| A61K 8/00 | (2006.01) |
| A61K 8/02 | (2006.01) |
| A61K 8/18 | (2006.01) |
| A61K 8/20 | (2006.01) |
| A61K 8/26 | (2006.01) |
| A61K 8/28 | (2006.01) |

(52) U.S. Cl. .......................................... 424/65; 424/68
(58) Field of Classification Search .................... 424/65, 424/68, 400, 401
See application file for complete search history.

(56) References Cited

U.S. PATENT DOCUMENTS

| | | | |
|---|---|---|---|
| 4,803,195 A | 2/1989 | Holzner | |
| 5,135,747 A | 8/1992 | Faryniarz et al. | |
| 5,176,903 A | 1/1993 | Goldberg et al. | |
| 5,378,468 A | 1/1995 | Suffis et al. | |
| 5,380,707 A | 1/1995 | Barr et al. | |
| 5,508,259 A | 4/1996 | Holzner et al. | |
| 5,626,856 A | 5/1997 | Berndt | |
| 5,711,941 A | 1/1998 | Behan et al. | |
| 5,780,020 A | 7/1998 | Petersen et al. | |
| 5,861,144 A | 1/1999 | Peterson et al. | |
| 5,861,146 A | 1/1999 | Peterson et al. | |
| 5,874,067 A | 2/1999 | Lucas et al. | |
| 5,879,666 A | 3/1999 | Lucas et al. | |
| 5,882,638 A | 3/1999 | Dodd et al. | |
| 5,885,599 A | 3/1999 | Peterson et al. | |
| 5,897,855 A | 4/1999 | Trinh et al. | |
| 5,932,198 A | 8/1999 | Goldman et al. | |
| 6,036,964 A | 3/2000 | Guenin et al. | |
| 6,110,449 A * | 8/2000 | Bacon et al. | 424/65 |
| 6,123,932 A | 9/2000 | Guskey et al. | |
| 6,150,542 A | 11/2000 | Acuna et al. | |
| 6,165,452 A | 12/2000 | Boden et al. | |
| 6,180,121 B1 | 1/2001 | Guenin et al. | |
| 6,187,301 B1 * | 2/2001 | Scavone et al. | 424/65 |
| 6,306,818 B1 | 10/2001 | Anderson et al. | |
| 6,375,938 B1 | 4/2002 | Clothier et al. | |
| 6,403,071 B1 | 6/2002 | Scavone et al. | |
| 6,495,097 B1 | 12/2002 | Streit et al. | |
| 6,509,010 B2 | 1/2003 | Beck et al. | |
| 6,793,915 B1 | 9/2004 | Guenin et al. | |
| 6,805,855 B2 | 10/2004 | Mattai et al. | |
| 6,835,373 B2 | 12/2004 | Kolodzik et al. | |
| 2003/0049290 A1 | 3/2003 | Jha et al. | |
| 2003/0087776 A1 | 5/2003 | Heltovics et al. | |
| 2003/0119713 A1 | 6/2003 | Heltovics et al. | |
| 2003/0194416 A1 | 10/2003 | Shefer et al. | |
| 2003/0198680 A1 | 10/2003 | Shefer et al. | |
| 2003/0198860 A1 | 10/2003 | Yasumoto | |
| 2003/0211125 A1 | 11/2003 | Heltovics et al. | |

(Continued)

FOREIGN PATENT DOCUMENTS

EP 0535942 A3 4/1993

(Continued)

OTHER PUBLICATIONS

Merriam-Webster's Collegiate Dictionary, 1996, Tenth Edition, 3 Page.*

(Continued)

*Primary Examiner* — James H. Alstrum-Acevedo
(74) *Attorney, Agent, or Firm* — Andrew J. Hagerty; Mark A. Charles

(57) ABSTRACT

Anhydrous, solid antiperspirant compositions comprising: (a) from about 0.1% to about 30% by weight of the composition, of a high-efficacy antiperspirant active; (b) from about 0.1% to about 35% by weight of the composition, of a thickening agent; (c) from about 10% to about 99% by weight of the composition, of an anhydrous liquid carrier; (d) from about 5 ppm to about 20% by weight of the composition, of a primary fragrance; and (e) from at least about 5 ppm by weight of the composition, of a secondary fragrance that is distinct from the primary fragrance and is included in a surfactant-free, water-releasable matrix, which renders the secondary fragrance within the matrix substantially odorless prior to aqueous activation, wherein the anhydrous, solid antiperspirant composition exhibits an Antiperspirant Efficacy Index of at least about 0.9, and wherein the anhydrous, solid antiperspirant composition is substantially devoid of a malodor reducing agent.

18 Claims, No Drawings

U.S. PATENT DOCUMENTS

| | | |
|---|---|---|
| 2003/0230205 A1 | 12/2003 | Mutschler et al. |
| 2003/0232025 A1 | 12/2003 | Colwell et al. |
| 2004/0001891 A1 | 1/2004 | Smith et al. |
| 2004/0091435 A1 | 5/2004 | Shefer et al. |
| 2004/0109833 A1 | 6/2004 | Tang et al. |
| 2004/0175346 A1 | 9/2004 | Guenin et al. |
| 2004/0175404 A1 | 9/2004 | Shefer et al. |
| 2004/0202632 A1 | 10/2004 | Gott et al. |
| 2005/0003975 A1 | 1/2005 | Browne et al. |
| 2006/0263311 A1 | 11/2006 | Scavone et al. |
| 2006/0263312 A1 | 11/2006 | Scavone et al. |
| 2006/0263313 A1 | 11/2006 | Scavone et al. |
| 2006/0292098 A1 | 12/2006 | Scavone et al. |
| 2007/0248552 A1 | 10/2007 | Scavone et al. |
| 2007/0248553 A1 | 10/2007 | Scavone et al. |

FOREIGN PATENT DOCUMENTS

| | | |
|---|---|---|
| EP | 0535942 B1 | 2/1999 |
| EP | 0965326 A1 | 12/1999 |
| EP | 0816322 B1 | 3/2003 |
| EP | 0966258 B1 | 5/2003 |
| JP | 2001316219 A | 11/2001 |
| WO | WO 98/18439 | 5/1998 |
| WO | WO 98/56340 | 12/1998 |
| WO | WO 03/088933 A1 | 10/2003 |
| WO | WO 2004/000254 A1 | 12/2003 |
| WO | WO 2004/000255 A1 | 12/2003 |
| WO | WO2004/078154 A1 | 9/2004 |

OTHER PUBLICATIONS

Chemical Abstracts Registry entry for Amberonne, accessed on Feb. 4, 2011.*
Labows, J. N. et al. "Axillary Odor Determination, Formation, and Control" in Antiperspirants and Deodorants, 2nd edition, Karl Laden, editor, Marcel Dekker, Inc.: New York, 1999, pp. 59-82.*
U.S. Appl. No. 11/712,775, filed Mar. 1, 2007, Scavone et al.
USPTO Office Action with mail date Nov. 13, 2008 from co-pending U.S. Appl. No. 11/132,823; 29 pages.
USPTO Office Action rejections/objections with mailed date Nov. 11, 2008 from co-pending U.S. Appl. No. 11/418,635; 24 pages.
USPTO Office Action rejections/objections with mail date Dec. 16, 2008 from co-pending U.S. Appl. No. 11/712,775; 18 pages.
USPTO Office Action rejections/objections with mail date Nov. 14, 2008 from co-pending U.S. Appl. No. 11/132,824; 32 pages.
USPTO Office Action rejections/objections with mail date Jan. 7, 2009 from co-pending U.S. Appl. No. 11/418,607; 17 pages.
USPTO Office Action rejections/objections with mail date Feb. 23, 2008 from co-pending U.S. Appl. No. 11/712,775; 15 pages.
USPTO Office Action rejections/objections with mail date Feb. 24, 2009 from co-pending U.S. Appl. No. 11/418,607; 12 pages.
Office Action pertaining to U.S. Appl. No. 11/132,823 dated Sep. 25, 2007—Co-pending application.
Office Action pertaining to U.S. Appl. No. 11/132,823 dated Jan. 30, 2008—Co-pending application.
Office Action pertaining to U.S. Appl. No. 11/132,823 dated Apr. 28, 2009—Co-pending application.
Office Action pertaining to U.S. Appl. No. 11/132,823 dated Sep. 28, 2009—Co-pending application.
Office Action pertaining to U.S. Appl. No. 11/418,635 dated Sep. 25, 2007—Co-pending application.
Office Action pertaining to U.S. Appl. No. 11/418,635 dated Jan. 30, 2008—Co-pending application.
Office Action pertaining to U.S. Appl. No. 11/418,635 dated Nov. 14, 2008—Co-pending application.
Office Action pertaining to U.S. Appl. No. 11/418,635 dated May 11, 2009—Co-pending.
Office Action pertaining to U.S. Appl. No. 11/418,635 dated Sep. 25, 2009—Co-pending.
Office Action pertaining to U.S. Appl. No. 11/712,775 dated Jan. 31, 2008—Co-pending.
Office Action pertaining to U.S. Appl. No. 11/712,775 dated Jul. 8, 2008—Co-pending.
Office Action pertaining to U.S. Appl. No. 11/712,775 dated Feb. 23, 2009—Co-pending application.
Office Action pertaining to U.S. Appl. No. 11/712,775 dated Oct. 5, 2009—Co-pending application.
Office Action pertaining to U.S. Appl. No. 11/132,824 dated Sep. 25, 2007—Co-pending application.
Office Action pertaining to U.S. Appl. No. 11/132,824 dated Jan. 30, 2008—Co-pending application.
Office Action pertaining to U.S. Appl. No. 11/132,824 dated Apr. 29, 2009—Co-pending application.
Office Action pertaining to U.S. Appl. No. 11/132,824 dated Sep. 25, 2009—Co-pending application.
Office Action pertaining to U.S. Appl. No. 11/418,607 dated Sep. 25, 2007—Co-pending application.
Office Action pertaining to U.S. Appl. No. 11/418,607 dated Jan. 30, 2008—Co-pending application.
Office Action pertaining to U.S. Appl. No. 11/418,607 dated Jul. 2, 2008—Co-pending application.
Office Action pertaining to U.S. Appl. No. 11/418,607 dated Feb. 24, 2009—Co-pending application.
Office Action pertaining to U.S. Appl. No. 11/418,607 dated Dec. 28, 2009—Co-pending application.
PCT/US2006/016092 International Search Report dated Aug. 11, 2006.
PCT/US2006/016092 International Search Report dated Oct. 5, 2006.
USPTO Office Action rejections/objections from co-pending U.S. Appl. No. 11/132,823; 14 pages, Jan. 30, 2008.
USPTO Office Action rejections/objections from co-pending U.S. Appl. No. 11/418,635; 14 pages, Jan. 30, 2008.
USPTO Office Action rejections/objections from co-pending U.S. Appl. No. 11/712,775; 23 pages, Jul. 8, 2008.
USPTO Office Action rejections/objections from co-pending U.S. Appl. No. 11/132,824; 14 pages, Jan. 30, 2008.
USPTO Office Action rejections/objections from co-pending U.S. Appl. No. 11/418,607; 17 pages, Jul. 2, 2008.

* cited by examiner

CONSUMER NOTICEABLE IMPROVEMENT IN WETNESS PROTECTION USING SOLID ANTIPERSPIRANT COMPOSITIONS

CROSS REFERENCE TO RELATED APPLICATION

This application is a continuation-in-part of U.S. application Ser. No. 11/418,607, filed May 5, 2006, which is a continuation-in-part of U.S. application Ser. No. 11/132,824, filed May 19, 2005 in the names of Scavone et al.

TECHNICAL FIELD

The present invention relates to solid antiperspirant compositions that provide to the consumer noticeable improvements in wetness protection via fragrance character shifts.

BACKGROUND OF THE INVENTION

Many different antiperspirant products are known for use in controlling or inhibiting underarm perspiration wetness and odor. These products are available in a variety of product forms such as solid sticks, soft solids or creams, roll-on liquids and aerosol or non-aerosol sprays. Most of these products have a base formula that contains an antiperspirant active such as an aluminum and or zirconium salt, a suspending or thickening agent, and a suitable liquid carrier. Many antiperspirant products are formulated to provide good wetness and odor protection. It has become increasingly difficult, however, to provide improvements in wetness protection that consumers notice. Even when substantial improvements in clinical wetness protection are provided, consumers may not see or notice the improvement.

Surprisingly, it has now been found that by providing high clinical efficacy antiperspirants in combination with a malodor reducing agent and a fragrance character shifting agent, consumers can perceive and appreciate improved wetness protection. The present invention provides high clinical efficacy, solid antiperspirant compositions that deliver consumer-perceived improvement in wetness protection.

SUMMARY OF THE INVENTION

In accordance with one of the preferred embodiments, there has now been provided an anhydrous, solid antiperspirant composition comprising: (a) from about 0.1% to about 30% by weight of the composition, of a high-efficacy antiperspirant active; (b) from about 0.1% to about 35% by weight of the composition, of a thickening agent; (c) from about 10% to about 99% by weight of the composition, of an anhydrous liquid carrier; (d) from about 5 ppm to about 20% by weight of the composition, of a primary fragrance; and (e) from at least about 5 ppm by weight of the composition, of a secondary fragrance that is distinct from the primary fragrance and is included in a surfactant-free, water-releasable matrix, which renders the secondary fragrance within the matrix substantially odorless prior to aqueous activation, wherein the anhydrous, solid antiperspirant composition exhibits an Antiperspirant Efficacy Index of at least about 0.9, and wherein the anhydrous, solid antiperspirant composition is substantially devoid of a malodor reducing agent.

DETAILED DESCRIPTION OF THE INVENTION

The solid antiperspirant compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

All percentages, parts and ratios are based upon the total weight of the topical compositions of the present invention and all measurements made are at 25° C., unless otherwise specified. All such weights as they pertain to listed ingredients are based on the active level and, therefore, do not include carriers or by-products that may be included in commercially available materials, unless otherwise specified.

The term "anhydrous" as used herein, unless otherwise specified, refers to those materials or compositions that are substantially free of added water. As it pertains to the compositions of the present invention, this means that the compositions are essentially free of added water. The term "anhydrous", however, as used herein can also mean that the composition contains water but that the water is isolated. The term "anhydrous" as used herein generally means that the material or composition preferably contains less than about 1%, less than about 0.5%, or zero percent, by weight of free or added water.

The term "particulate", as used herein, refers to compositions or materials that are comprised of solid particles and are not dissolved in water or other solvents.

As used herein, the term "cosmetically acceptable", as used herein, means that the product glides on smoothly during application, is non-irritating, and results in little or no visible residue (e.g. low residue performance) after application to the skin.

As used herein, the term "water-releasable" refers to the release of the secondary fragrance from the matrix upon aqueous activation so that it is detectable.

As used herein, the term "solid antiperspirant compositions" includes solid and semi-solid antiperspirant compositions.

I. Product Characteristics

The solid antiperspirant compositions of the present invention are defined in terms of an essential combination of ingredients and product characteristics, wherein the product characteristics include product hardness, Residue Grade, Tan Delta values, and/or Antiperspirant Efficacy Index. Each of these product characteristics is defined hereinafter in detail.

Hardness

Solid antiperspirant compositions of the present invention may have a product hardness of from at least about 600 gram·force, from about 750 gram·force, or from about 800 gram·force but no more than about 5,000 gram·force, from about 2,000 gram·force, or from about 1,400 gram·force.

The term "product hardness" or "hardness" as used herein is a reflection of how much force is required to move a penetration cone a specified distance and at a controlled rate into a solid antiperspirant composition under the following test conditions. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the peak force required to move a standard 45° angle penetration cone through the composition for a distance of 10 mm at a rate of 2 mm/second. The standard cone is available from Texture Technology Corp., as part number TA-15, and has a total cone length of about 24.7 mm, angled cone length of about 18.3 mm, a maximum diameter of the angled surface of the cone of about 15.5 mm. The cone is a smooth, stainless steel construction and weighs about 17.8 grams.

The product hardness may be selected for each solid antiperspirant composition to help provide the desired application rheology, thus resulting in the desired low-residue application layer as applied to the skin. Although low-residue performance can be controlled by a variety of mechanisms known in the antiperspirant art, the compositions of the present invention may exhibit low-residue performance, at least in part, by controlling product hardness.

Residue Grade

The solid antiperspirant compositions of the present invention provide low residue performance. These compositions may have a Residue Grade of less than about 50, than about 40, or less than about 35. In this context, the Residue Grade is an indirect measure of the visible residue that is likely to remain on the skin after topical application of the solid antiperspirant composition.

The Residue Grade is determined by the Naugahyde Method. In accordance with this method, a piece of commercial, black, dull finished, small grained vinyl (Boltaflex vinyl upholstery, Prefixx protective finish, Mfr. GenCorp Polymer Products) cut to a 10 cm×15 cm rectangular strip is placed on a horizontal platform. Each corner of the vinyl strip is then secured with a small binder clip after the material has been slightly stretched to create a smooth surface. A solid antiperspirant composition under ambient conditions (for at least 24 hours prior to testing) is trimmed flat across the top of the container and placed on a balance which is then tared to 0.00 grams in order to determine the mass of product to be applied to the vinyl. The solid antiperspirant composition contained within and partially extending out 0.5 cm from a conventional solid antiperspirant package (5.2 cm×2.7 cm topographically oval package) is positioned perpendicular to and above the positioned vinyl by securing the container onto a movable mechanical arm, such that the flat, trimmed surface of the secured product extends out of the package and is facing parallel to the horizontally positioned vinyl. The solid antiperspirant composition is then slowly moved vertically toward the vinyl sample until the flat, trimmed surface of the product rests upon the far left area of the positioned vinyl. A weight is placed on the product sample so that the entire flat, trimmed surface of the product uniformly contacts the positioned vinyl during testing. The applied weight is selected so as to provide 45.3 grams/cm$^2$ to the trimmed surface of the product sample, e.g., 500 gram weight applied to an oval 5.2 cm×2.7 cm trimmed surface area. The weighted sample is then manually moved repeatedly back and forth across the entire length of the piece of vinyl at a rate of one stroke per second (one stroke equals one left to right movement or one right to left movement), until 0.20 gms.±0.02 gm. of product has been evenly applied over 15.24 cm×5.08 cm area of the black vinyl (0.0026 grams of product per cm$^2$ of the black vinyl surface). The product sample is then removed from the mechanical arm piece and weighed. The vinyl is then unclipped and carefully removed from the platform and dried down for 6 hours.

A calibrated Minolta CR-300 Chroma Meter (available from Minolta Corp., Ramsey, N.J., USA) is then used to measure the L-value (on the L, a, b color scale) of each of the applied vinyl surfaces. For each of the applied vinyl surfaces, twelve random, non-overlapping areas of the applied surface are measured for L-values by the Chroma Meter with its clear plastic view port removed to allow direct placement of the Meter port onto the vinyl so that the meter port is positioned over but without touching the applied vinyl surface. An average L-value is then determined for the twelve measurements which then corresponds to the Residue Grade as described herein.

Tan Delta

The solid antiperspirant compositions of the present invention preferably have mechanical properties defined in terms of selected Tan Delta values, wherein the compositions have a Tan Delta Value at 1 Hz of less than about 0.40, less than about 0.35, or less than about 0.30. These Tan Delta values are measured by Dynamic Mechanic Thermal Analysis (DMTA) in accordance with the following methodology.

The Tan Delta value as used herein is determined by Dynamic Mechanical Thermal Analysis (DMTA). In this analysis, a solid antiperspirant composition is subjected to a slight two-dimensional vertical force comprised of a static (constant) and dynamic (oscillating) component. Enough dynamic force is applied to generate about 5 microns of spring amplitude before measuring how the antiperspirant stick structure responds as a function of the applied force, temperature or frequency changes. DMTA is used to determine a storage modulus value and a ratio of a loss modulus to storage modulus (Tan Delta value).

More specifically, Tan Delta values may be measured using a Perkin Elmer Dynamic Mechanical Thermal Analysis (DMTA) instrument, Model DMA 7e, (available from Perkin Elmer Corporation, 761 Main Avenue, Norwalk, Conn., USA), fitted with a parallel plate fixture. The top plate (connected to the probe) is a 10 mm plate, while the bottom plate (on which the sample rests) is a 20 mm plate. The instrument is calibrated according to manufacturer instructions. The probe is calibrated using the Tare Probe function on the Pyris software. The sample is prepared by cutting from an antiperspirant stick a 6 mm (thick) by 10 mm wide section. The sample must be cut from the stick so that the sample thickness is uniformly 6 mm to obtain reliable and consistent measures. The cross section is then placed into the DMTA instrument into the parallel plate fixture arrangement, resting on the 20 mm plate. The probe is lowered (with no force applied) and the furnace is raised with the temperature set at 25° C. The forces are set as such: A static force of 1000 nm (milliNewton) and a dynamic force of 800 nm (milliNewton) are used as the initial force at a constant frequency of 1 cycle/second (Hz). The constant amplitude function is set to maintain a constant amplitude of about 5 microns, allowing the dynamic component to vary to meet this amplitude setting. If required (i.e. the dynamic component exceeds the static force and causes the probe to bounce), the static force range should be adjusted so that the DMTA can control the instrument at a constant about 5 microns of amplitude. The capturing of the Tan Delta measurement should be started within one minute after applying the force component. The Tan Delta is then recorded over the space of 5 minutes. This is repeated with 5 different samples of the same material and the average recorded. This average value is then reported as the Tan Delta value as used herein.

It has been found that the solid antiperspirant compositions of the present invention are especially effective in providing low residue performance and aesthetics when formulated to have the above-defined Tan Delta Values. These compositions, when formulated within the defined range of Tan Delta values, may apply more smoothly and with relatively less visible residue.

Antiperspirant Efficacy Index

The solid antiperspirant compositions of the present invention provide improved antiperspirant efficacy wherein the composition exhibits an Antiperspirant Efficacy Index of at least about 0.9 as determined by the methodology described in U.S. Pat. No. 6,352,688, issued to Scavone, et al on Mar. 5, 2002.

The Antiperspirant Efficacy Index is calculated as the weight ratio of the amount (mg) of sweat collected from the control treatment side of a participant to the amount of sweat collected from the test product treatment side of that same participant. As used herein and in accordance with the methodology, the term "Antiperspirant Efficacy Index" refers to the 3-day and/or the 10-day Antiperspirant Efficacy Index.

It has been found that the 10-day Antiperspirant Index of the high efficacy antiperspirant actives of the present invention may be from at least about 0.9, at least about 1.0 or at least about 1.1. The 3-day Antiperspirant Index of the high efficacy antiperspirant actives of the present invention may be from at least about 1.0, at least about 1.1, or at least about 1.2. The ratio of the Antiperspirant Index at 3-days and 10-days may be at least about 0.9, at least about 1.0, or at least about 1.1. Unlike many other antiperspirant products that require several days of repeated use to develop optimal antiperspirant efficacy, it has been found that the actives of the present invention provide improved antiperspirant efficacy after 3-days of continuous daily application than many other highly effective products and product forms after the same period of application.

High C log P Liquids

The solid antiperspirant compositions of the present invention may be substantially free of all organic nonvolatile liquids having a C log P value greater than about 5.5, greater than about 6.5, or greater than about 7.0.

In this context, the term "substantially free" means that the compositions may contain a sufficiently low concentration of the high C log P organic nonvolatile liquids so that antiperspirant efficacy and/or release is not inhibited. The term "substantially free" also means that the compositions comprise less than about 5%, less than about 2%, less than about 1%, or zero percent, by weight of the high C log P organic nonvolatile liquids in the solid antiperspirant composition. The term "organic liquid" means non-silicone containing materials that are liquid at or below human skin temperature under ambient conditions, or which are otherwise in liquid form at or below human skin temperature once formulated into the finished anhydrous solid antiperspirant composition of the present invention.

It has been found that the antiperspirant efficacy of the solid antiperspirant compositions of the present invention may be significantly enhanced by maintaining an anhydrous matrix that is substantially free of any nonvolatile organic material that is liquid at or below human skin temperature (37° C.), and which has a relatively high C log P value. It is believed that these materials can hamper dissolution and release of antiperspirant active into sweat ducts after topical application to the skin.

Non limiting examples of organic, high C log P, nonvolatile liquids that are substantially absent from the present invention may include mineral oil, PPG-14 butyl ether, isopropyl myristate, butyl stearate, cetyl octanoate, butyl myristate, C12-15 alkylbenzoate (e.g., Finsolv™), octyldodecanol, isostearyl isostearate, octododecyl benzoate, isostearyl lactate, isostearyl palmitate, and isobutyl stearate. The compositions of the present invention may be substantially free of all nonvolatile, organic liquids that are esters, hydrocarbons, hydroxy substituted hydrocarbons, and combinations thereof, which have the high C log P values described herein.

It has been found that the solid antiperspirant compositions of the present invention are preferably substantially free of these high C log P, nonvolatile, organic liquids but that high C log P organic materials can be used in the compositions provided that such materials are solids at or below human skin temperature (37° C.) or that such materials are physically or chemically partitioned away from the antiperspirant active in the composition, such as by encapsulation. It has been found that such solids or otherwise partitioned materials do not have the same negative effect on antiperspirant efficacy as do the high C log P, nonvolatile, organic liquids described herein.

The use of C log P values is well known in the chemical arts as a calculated value that represents the relative affinity that a material has for partitioning between octanol and water, so that a material that partitions more readily into octanol would tend to be more lipophillic and have a higher C log P value than a material that partitions less readily into octanol. For purposes of defining the solid antiperspirant compositions of the present invention, C log P values are obtained from or calculated by the methods described in Handbook of Physical Properties of Organic Chemicals, Edited by Philip H. Howard and William M. Meylan, CRC Press-Lewis Publishers, 1997.

C log P values can also be determined by the Pamona Med Chem/Daylight "C LOG P" program, Version 4.42, available from Biobyte Corporation, Claremont, Calif. Other suitable methods for determining C log P values include the fragment approach described by Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990), which description is incorporated herein by reference. Still other suitable methods are described or provided by Daylight Information Systems, Mission Viejo, Calif., Daylight V4.61, Algorithm: V3.05, Database: V16. General information pertaining to C log P values and methodologies are described in Chemical Reviews, 93(4), 1993, 1281-1306. As used herein, C log P values include calculated and measured log P values.

The nonvolatile, high C log P, organic liquids may include materials that are solid under ambient conditions but that are at least partially melted and in liquid form at or below human skin temperature (37° C.) or which are otherwise in liquid form in the antiperspirant composition as applied topically to the skin. In this context, a material is determined to be liquid at or below human skin temperature by evaluating the material in a finished antiperspirant composition using Differential Scanning Calorimetry (DSC). For example, A Perkin Elmer Model DSC-7 manufactured by Perkin Elmer Corporation, 761 Main Street, Norwalk Conn., can be used to measure a melting profile of the desired material This is done by preparing a 20 mg sample in a volatile sample pan arrangement of the desired finished product to be tested. The heating curve is generated at 5° C./min and is analyzed by measuring the partial area that melts below 37° C., and those showing at least 10% of the DSC curve below 37° C. are "liquids" for purposes of defining the term "organic liquids" herein.

II. Composition

Antiperspirant Active

The solid antiperspirant compositions of the present invention may comprise an antiperspirant active suitable for application to human skin. The concentration of the antiperspirant active in the composition should be sufficient to provide the desired enhanced wetness protection that is perceivable by the user. For example, the active may be present in an amount of from at least about 0.1%, at least about 0.5%, or at least about 1%, at least about 5% but no more than about 60%, no more than about 35%, no more than about 25% or no more than about 20%, by weight of the composition. These weight percentages are calculated on an anhydrous metal salt basis exclusive of water and any complexing agents such as glycine, glycine salts, or other complexing agents. The antiperspirant active as formulated in the composition are in the form of dispersed particulate solids having an average particle size or diameter of less than about 100 µm, less than about 20 µm, or less than about 10 µm.

Compositions of the present invention may include any compound, composition or other material having antiperspirant activity. Such actives may include astringent metallic salts, especially inorganic and organic salts of aluminum, zirconium and zinc, as well as mixtures thereof. For example, the antiperspirant actives may include zirconium-containing salts or materials, such as zirconyl oxyhalides, zirconyl hydroxyhalides, and mixtures thereof; and/or aluminum-containing salts such as, for example, aluminum halides, aluminum chlorohydrate, aluminum hydroxyhalides, and mixtures thereof.

1. Aluminum Salts

Aluminum salts useful in the present invention include those that conform to the formula:

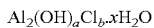

$$Al_2(OH)_aCl_b \cdot xH_2O$$

wherein a is from about 2 to about 5; the sum of a and b is about 6; x is from about 1 to about 6; where a, b, and x may have non-integer values. For example, aluminum chlorohydroxides referred to as "5/6 basic chlorohydroxide," wherein a is about 5 and "2/3 basic chlorohydroxide", wherein a=4 may be used.

Processes for preparing aluminum salts are disclosed in U.S. Pat. No. 3,887,692, issued to Gilman on Jun. 3, 1975; U.S. Pat. No. 3,904,741, issued to Jones et al. on Sep. 9, 1975; and U.S. Pat. No. 4,359,456 issued to Gosling et al. on Nov. 16, 1982. A general description of these aluminum salts can also be found in *Antiperspirants and Deodorants*, Cosmetic Science and Technology Series Vol. 20, $2^{nd}$ edition, edited by Karl laden. Mixtures of aluminum salts are described in British Patent Specification 1,347,950, filed in the name of Shin et al. and published Feb. 24, 1974.

2. Zirconium Salts

Zirconium salts for use in the present invention include those which conform to the formula:

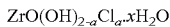

$$ZrO(OH)_{2-a}Cl_a \cdot xH_2O$$

wherein a is from about 1.5 to about 1.87; x is from about 1 to about 7; and wherein a and x may both have non-integer values. These zirconium salts are described in Belgian Patent 825,146, issued to Schmitz on Aug. 4, 1975. Useful to the present invention are zirconium salt complexes that additionally contain aluminum and glycine, commonly known as "ZAG complexes". These complexes contain aluminum chlorohydroxide and zirconyl hydroxy chloride conforming to the above-described formulas. Such ZAG complexes are described in U.S. Pat. No. 4,331,609, issued to Orr on May 25, 1982 and U.S. Pat. No. 4,120,948, issued to Shelton on Oct. 17, 1978.

Malodor Reducing Agent

The present invention may comprise a malodor reducing agent. Malodor reducing agents include components other than the antiperspirant active within the composition that act to eliminate the effect that body odor has on fragrance display. These agents may combine with the offensive body odor so that they are not detectable including, but not limited to, suppressing evaporation of malodor from the body, absorbing sweat or malodor, masking the malodor or microbiological activity on odor causing organisms. The concentration of the malodor reducing agent within the composition is sufficient to provide such chemical or biological means for reducing or eliminating body odor. Although the concentration will vary depending on the agent used, generally, the malodor reducing agent may be included within the composition from at least about 0.05%, at least about 0.5%, or at least about 1% but no more than about 15%, no more than about 10% or no more than about 6%, by weight of the composition.

Malodor reducing agents of the present invention may include, but are not limited to, pantothenic acid and its derivatives, petrolatum, menthyl acetate, uncomplexed cyclodextrins and derivatives thereof, talc, silica and mixtures thereof. Such agents may be used as described in U.S. Pat. No. 6,495,149, issued to Scavone, et al and US patent application 2003/0152539, filed Jan. 25, 2002 in the names of Scavone, et al.

For example, if panthenyl triacetate is used, the concentration of the malodor reducing agent may be from at least about 0.1% or about 0.25% but no more than about 3.0% or about 2.0%, by weight of the composition. Another example of a malodor reducing agent is petrolatum which may be included from about 0.10% or 0.5% but no more than about 15% or about 10%, by weight of the composition. A combination may also be used as the malodor reducing agent including, but not limited to, panthenyl triacetate and petrolatum at levels from about 0.1% or 0.5% but no more than about to 3.0% or about 10%, by weight of the composition. Menthyl acetate, a derivative of menthol that does not have a cooling effect, may be included from about 0.05% or 0.01% but no more than about 2.0% or no more than about 1.0%, by weight of the composition. The malodor reducing agent of the present invention may be in the form of a liquid or a semi-solid such that it does not contribute to product residue.

In accordance with one embodiment, compositions of the present invention are substantially devoid of a malodor reducing agent; that is, the composition contains less than 0.05%, by weight, of a malodor reducing agent.

Suspending/Thickening Agent

The solid antiperspirant compositions of the present invention also comprise thickening agents to help provide the composition with the desired viscosity, rheology, texture and/or product hardness, or to otherwise help suspend any dispersed solids or liquids within the composition. The term "thickening agent" may include any material known or otherwise effective in providing suspending, gelling, viscosifying, solidifying or thickening properties to the composition or which otherwise provide structure to the final product form. These thickening agents may include gelling agents, polymeric or nonpolymeric agents, inorganic thickening agents, or viscosifying agents. The thickening agents may include organic solids, silicone solids, crystalline or other gellants, inorganic particulates such as clays or silicas, or combinations thereof.

The concentration and type of the thickening agent selected for use in the antiperspirant composition of the present invention will vary depending upon the desired product form, viscosity, and hardness. The thickening agents suitable for use herein, may have a concentration range from at least about 0.1%, at least about 3%, or at least about 5% but no more than about 35%, no more than about 20%, or no more than about 10%, by weight of the composition.

Non-limiting examples of suitable gelling agents of the present invention include fatty acid gellants, salts of fatty acids, hydroxyl acids, hydroxyl acid gellants, esters and amides of fatty acid or hydroxyl fatty acid gellants, cholesterolic materials, dibenzylidene alditols, lanolinolic materials, fatty alcohols, triglycerides, sucrose esters such as SEFA behenate, inorganic materials such as clays or silicas, other amide or polyamide gellants, and mixtures thereof. Concentrations of all such gelling agents may be from at least about 0.1%, at least about 1%, or at least about 5% and no more than about 25%, no more than about 15%, or no more than about 10%, by weight of the composition.

Suitable gelling agents include fatty acid gellants such as fatty acid and hydroxyl or alpha hydroxyl fatty acids, having from about 10 to about 40 carbon atoms, and ester and amides of such gelling agents. Non-limiting examples of such gelling agents include, but are not limited to, 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred gelling agents are 12-hydroxystearic acid, esters of 12-hydroxystearic acid, amides of 12-hydroxystearic acid and combinations thereof.

Other suitable gelling agents include amide gellants such as disubstituted or branched monoamide gellants, monsubstituted or branched diamide gellants, triamide gellants, and combinations thereof, including n-acyl amino acid derivatives such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816, issued Jul. 4, 1995, and U.S. Pat. No. 5,840,287, filed Dec. 20, 1996.

Still other examples of suitable gelling agents include fatty alcohols having at least about 8 carbon atoms, at least about 12 carbon atoms but no more than about 40 carbon atoms, no more than about 30 carbon atoms, or no more than about 18 carbon atoms. For example, fatty alcohols include but are not limited to cetyl alcohol, myristyl alcohol, stearyl alcohol and combinations thereof.

Non limiting examples of suitable tryiglyceride gellants include tristearin, hydrogenated vegetable oil, trihydroxysterin (Thixcin® R, available from Rheox, Inc.), rape seed oil, castor wax, fish oils, tripalmitin, Syncrowax® HRC and Syncrowax® HGL-C (Syncrowax® available from Croda, Inc.).

Other suitable thickening agents include waxes or wax-like materials having a melt point of above 65° C., more typically from about 65° C. to about 130° C., examples of which include, but are not limited to, waxes such as beeswax, carnauba, bayberry, candelilla, montan, ozokerite, ceresin, hydrogenated castor oil (castor wax), synthetic waxes and microcrystalline waxes. Castor wax is preferred within this group. Other high melting point waxes are described in U.S. Pat. No. 4,049,792, Elsnau, issued Sep. 20, 1977.

Further thickening agents for use in the solid antiperspirant compositions of the present invention may include inorganic particulate thickening agents such as clays and colloidal pyrogenic silica pigments. For example, colloidal pyrogenic silica pigments such as Cab-O-Sil®, a submicroscopic particulated pyrogenic silica may be used. Other known or otherwise effective inorganic particulate thickening agents that are commonly used in the art can also be used in the solid antiperspirant compositions of the present invention. Concentrations of particulate thickening agents may range, for example, from at least about 0.1%, at least about 1%, at least about 5% but no more than about 35%, no more than about 15%, no more than about 10% or no more than about 8%, by weight of the composition.

Suitable clay thickening agents include montmorillonite clays, examples of which include bentonites, hectorites, and colloidal magnesium aluminum silicates. These and other suitable clays may be hydrophobically treated, and when so treated will generally be used in combination with a clay activator. Non-limiting examples of suitable clay activators include propylene carbonate, ethanol, and combinations thereof. When clay activators are present, the amount of clay activator will typically range from at least about 40%, at least about 25%, at least about 15% but no more than about 75%, no more than about 60%, or no more than about 50%, by weight of the clay.

Anhydrous Liquid Carrier

The solid antiperspirant compositions of the present invention may comprise anhydrous liquid carriers at concentrations ranging from at least about 10%, at least about 15%, at least about 20%, at least about 25% but no more than about 99%, no more than about 70%, no more than about 60% or no more than about 50%, by weight of the composition. Such concentrations will vary depending upon variables such as product form, desired product hardness, and selection of other ingredients in the composition. The anhydrous carrier may be any anhydrous carrier known for use in personal care applications or otherwise suitable for topical application to the skin. For example, anhydrous carriers of the present invention may include, but are not limited to volatile and nonvolatile fluids.

A. Volatile Fluid

The antiperspirant composition of the present invention may further comprise a volatile fluid such as a volatile silicone carrier whose concentration may be from about 20% or from about 30% but no more than about 80% or no more than about 60%, by weight of the composition. The volatile silicone of the solvent may be cyclic, linear, and/or branched chain silicone. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976).

The volatile silicone may be a cyclic silicone having from at least about 3 silicone atoms or from at least about 5 silicone atoms but no more than about 7 silicone atoms or no more than about 6 silicone atoms. For example, volatile silicones may be used which conform to the formula:

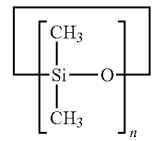

wherein n is from about 3 or from about 5 but no more than about 7 or no more than about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

B. Non-Volatile Fluid

The antiperspirant composition of the present invention may further comprise a non-volatile fluid. These non-volatile fluids may be either non-volatile organic fluids or non-volatile silicone fluids.

1. Non-Volatile Organic Fluids

The antiperspirant composition of the present invention may further comprise non-volatile organic fluids. The non-volatile organic fluid can be present at concentrations ranging from about 1%, from about 2% but no more than about 20% or no more than about 15%, by weight of the composition.

Non-limiting examples of nonvolatile organic fluids include, but are not limited to, mineral oil, PPG-14 butyl ether, isopropyl myristate, petrolatum, butyl stearate, cetyl octanoate, butyl myristate, myristyl myristate, C12-15 alkylbenzoate (e.g., Finsolv™), dipropylene glycol dibenzoate, PPG-15 stearyl ether benzoate and blends thereof (e.g. Finsolv TPP), neopentyl glycol diheptanoate (e.g. Lexfeel 7 supplied by Inolex), octyldodecanol, isostearyl isostearate, octododecyl benzoate, isostearyl lactate, isostearyl palmitate, isononyl/isononoate, isoeicosane, octyldodecyl neopentanate, hydrogenated polyisobutane, and isobutyl stearate. Many such other carrier liquids are disclosed in U.S. Pat. No. 6,013, 248 (Luebbe et al.) and U.S. Pat. No. 5,968,489 (Swaile et al).

2. Nonvolatile Silicone Fluids

The solid antiperspirant compositions of the present invention may further comprise a non-volatile silicone fluid. The non-volatile silicone fluid may be a liquid at or below human skin temperature, or otherwise in liquid form within the anhydrous antiperspirant composition during or shortly after topical application. The concentration of the non-volatile silicone may be from about 1%, from about 2% but no more than about 15% or no more than about 10%, by weight of the composition. Nonvolatile silicone fluids of the present invention may include those which conform to the formula:

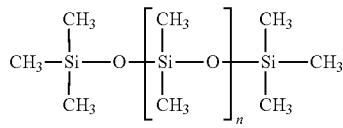

wherein n is greater than or equal to 1. These linear silicone materials may generally have viscosity values of from about 5 centistokes, from about 10 centistokes but no more than about 100,000 centistokes, no more than about 500 centistokes, no more than about 200 centistokes or no more than about 50 centistokes, as measured under ambient conditions.

Specific non limiting examples of suitable nonvolatile silicone fluids include Dow Corning 200, hexamethyldisiloxane, Dow Corning 225, Dow Corning 1732, Dow Corning 5732, Dow Corning 5750 (available from Dow Corning Corp.); and SF-96, SF-1066 and SF18(350) Silicone Fluids (available from G.E. Silicones).

Low surface tension non-volatile solvent may be also be used. Such solvents may be selected from the group consisting of dimethicones, dimethicone copolyols, phenyl trimethicones, alkyl dimethicones, alkyl methicones, and mixtures thereof. Low surface tension non-volatile solvents are also described in U.S. Pat. No. 6,835,373 (Kolodzik et al.).

Primary Fragrance

Solid antiperspirant compositions of the present invention may further comprise a primary fragrance to help cover or mask malodors resulting from perspiration, or which otherwise provide the compositions with the desired perfume or unscented/neutral aroma. The scented primary fragrance may include any perfume or perfume chemical suitable for topical application to the skin and suitable for use in antiperspirant compositions.

The concentration of the primary fragrance in the solid antiperspirant compositions of the present invention should be effective to provide the desired aroma including, but not limited to, unscented. As used herein, "unscented" refers to the level of fragrance wherein the level of fragrance is below 5 ppm such that the fragrance is absent or undetected. Generally, the concentration of the scented primary fragrance is from at least about 5 ppm, from about 0.1%, from about 0.5% but no more than about 20%, no more than about 10%, no more than about 5%, or no more than about 2%, by weight of the composition. The primary fragrance should not impart excessive stinging to the skin, especially broken or irritated skin, at the concentrations disclosed herein. The primary fragrance may be included in the solid antiperspirant compositions of the present invention as a free perfume.

Secondary Fragrance

The secondary fragrance of the present invention should be substantially different and distinct from the composition of the primary fragrance in order to overcome the effect of fragrance habituation and to make the second fragrance noticeable over the primary fragrance. Generally, solid antiperspirant compositions of the present invention may comprise from about 5 ppm, from about 0.1%, from about 0.5% but no more than about 20%, no more than about 10%, no more than about 5%, or no more than about 2%, by weight of the composition. The secondary fragrance should not impart excessive stinging to the skin, especially broken or irritated skin, at the concentrations disclosed herein.

Any perfume or perfume chemical suitable for topical application to the skin and suitable for use in antiperspirant compositions may be used as the secondary fragrance, however, it will not be included within the composition as a free perfume. The secondary fragrance will be included in a surfactant-free, water-releasable matrix, which renders the secondary fragrance within the matrix initially substantially odorless. The secondary fragrance may be selected from the group consisting of perfumes, highly volatile perfume materials having a boiling point of less than about 250° C., High Impact Accord perfume materials, and mixtures thereof. Such fragrances will be included within a matrix selected such as cyclodextrin complexes as described herein.

Perfumes

High Impact Accord (HIA) Perfumes

HIA perfume ingredients are characterized by their respective boiling point (B.P.), octanol/water partition coefficient (P) and odor detection threshold ("ODT"). The "octanol/water partition coefficient (P)" of a perfume ingredient is the ratio between its equilibrium concentrations in octanol and in water. The boiling points of many perfume ingredients, at standard pressure (760 mm Hg) are given in, e.g., "Perfume and Flavor Chemicals (Aroma Chemicals)," Steffen Arctander, published by the author.

The log P values of many perfume ingredients have been reported; for example, the Pomona92 database, available from Daylight Chemical Information Systems, Inc. (Daylight CIS), Irvine, Calif., contains many, along with citations to the original literature. However, the log P values are most conveniently calculated by the "C LOG P" program, also available from Daylight CIS. This program also lists experimental log P values when they are available in the Pomona92 database. The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each perfume ingredient, and takes into account the numbers and types of atoms, the atom connectivity, and chemical bonding. The C log P values, which are the most reliable and widely used estimates for this physicochemical property, are preferably used instead of the experimental log P values in the selection of perfume ingredients which are useful in the present invention.

Odor detection thresholds are determined using a gas chromotograph as disclosed in co-pending application, Browne, et al., filed Jun. 9, 2004.

For the first class of perfume ingredients, each Class 1 HIA perfume ingredient of this invention may have a B.P., determined at the normal, standard pressure of 760 mm Hg, of 275° C. or lower and an ODT of less than or equal to 50 parts per billion (ppb). Since the partition coefficients of the perfume ingredients of this invention may have high values, they are more conveniently given in the form of their logarithm to the base 10 log P. The perfume ingredients of this invention have a C log P of 2 and higher.

Table 1 gives some non-limiting examples of HIA perfume ingredients of Class 1.

TABLE 1

HIA Perfume Ingredients of Class 1
HIA Ingredients of Class 1

Ionone beta
4-(2,2,6-Trimethylcyclohex-1-enyl)-2-but-en-4-one
2,4-Decadienoic acid, ethyl ester (E,Z)-
6-(and -8) isopropylquinoline
Acetaldehyde phenylethyl propyl acetal
Acetic acid, (2-methylbutoxy)-, 2-propenyl ester
Acetic acid, (3-methylbutoxy)-, 2-propenyl ester
Benzaldehyde
2,6,10-Trimethyl-9-undecenal
Glycolic acid, 2-pentyloxy-, allyl ester
Hexanoic acid, 2-propenyl ester
1-Octen-3-ol
trans-Anethole
iso butyl (z)-2-methyl-2-butenoate
Anisaldehyde diethyl acetal
Benzenepropanal, 4-(1,1-dimethylethyl)-
2,6-Nonadien-1-ol
3-methyl-5-propyl-cyclohexen-1-one
Buranoic acid, 2-methyl-, 3-hexenyl ester, (Z)-
Acetaldehyde, [(3,7-dimethyl-6-octenyl)oxy]-
Lauronitrile
2,4-dimethyl-3-cyclohexene-1-carbaldehyde
2-Buten-1-one, 1-(2,6,6-trimethyl-1,3-cyclohexadien-1-yl)-
2-Buten-1-one, 1-(2,6,6-trimethyl-2-cyclohexen-1-yl)-, (E)-
Ethyl-2-Methyl Butyrate
gamma-Decalactone
trans-4-decenal
decanal
2-Pentylcyclopentanone
1-(2,6,6,Trimethyl 3 Cyclohexen-1-yl)-2 Buten-1-one)
2,6-dimethylheptan-2-ol
Benzene, 1,1'-oxybis-
4-Penten-1-one, 1-(5,5-dimethyl-1-cyclohexen-1-yl)-
Butanoic acid, 2-methyl-, ethyl ester
Ethyl anthranilate
2-Oxabicyclo[2.2.2]octane, 1,3,3-trimethyl-
2-6-nonadienal
Eugenol
Citralva Plus
Damarose Alpha
3-(3-isopropylphenyl)butanal
methyl 2-octynoate
Decyl Aldehyde
Methyl-2-nonenoate
4-(2,6,6-trimethyl-1-cyclohexen-1-yl)-3-buten-2-one
Pyrazine, 2-methoxy-3-(2-methylpropyl)-
Quinoline, 6-secondary buty
Isoeugenol
Mandarin Aldehyde
Oxane
2H-Pyran-2-one, tetrahydro-6-(3-pentenyl)-
Cis-3-Hexenyl Methyl Carbonate
Linalool
1,6,10-Dodecatriene, 7,11-dimethyl-3-methylebe-, (E)-
2,6-dimethyl-5-heptenal
4,7 Methanoindan 1-carboxaldehyde, hexahydro
2-methylundecanal
Methyl 2-nonynoate TABLE 1-continued HIA Perfume Ingredients of Class 1
HIA Ingredients of Class 1

1,1-dimethoxy-2,2,5-trimethyl-4-hexene
melonal
Methyl Nonyl Acetaldehyde
Undecalactone
Trans-2-Hexanal
Pino Acetaldehyde
Neobutenone
Benzoic acid, 2-hydroxy-, methyl ester
4-Penten-1-one, 1-(5,5-dimethyl-1-cyclohexen-1-yl)
2H-Pyran, 3,6-dihydro-4 methyl-2-(2-methyl-1-propenyl)-
2,6-Octadienenitrile, 3,7-dimethyl-, (Z)-
2,6-nonadienal
6-Nonenal, (Z)-
nonanal
octanal
2-Nonenenitrile
Acetic acid, 4-methylphenyl ester
Gamma Undecalactone
2-norpinene-2-propionaldehyde 6,6 dimethyl
4-nonanolide
9-decen-1-ol
2H-Pyran, tetrahydro-4-methyl-2-(2-methyl-1-propenyl)-
5-methyl-3-heptanone oxime
Octanal, 3,7-dimethyl-
4-methyl-3-decen-5-ol
10-Undecen-1-al
Pyridine, 2-(1-theylpropyl)-
Spiro[furan-2(3H),5'[4,7]methanol[5H]indene], decahydro-
Anisic Aldehyde
Flor Acetate
Rose Oxide
Cis 3 Hexenyl Salicylate
Methyl Octin Carbonate
Ethyl-2-Methyl Butyrate The secondary fragrance of the invention may also comprise one or more HIA perfume ingredients of Class 1.

Class 1 HIA perfume ingredients are very effusive and very noticeable when included in a composition. Of the perfume ingredients in a given perfume composition, from at least about 15% to about 75% or to about 50%, by weight of the composition, are Class 1 HIA perfume ingredients.

The secondary fragrance of the invention may also comprise one or more HIA perfume ingredients of Class 2.

Class 2 HIA perfume ingredients leave a lingering scent on the skin. Of the perfume ingredients in a given perfume composition, from at least about 0.01% to about 30% or to about 25%, by weight of the composition, are Class 2 HIA perfume ingredients.

For the second class of perfume ingredients, each Class 2 HIA perfume ingredient of this invention has a B.P., determined at the normal, standard pressure of about 760 mm Hg, of greater than 275° C. and an ODT of less than or equal to 50 parts per billion (ppb). Since the partition coefficients of the perfume ingredients of this invention have high values, they are more conveniently given in the form of their logarithm to the base 10 log P. The perfume ingredients of this invention have a C log P of at least about 4.

Table 2 gives some non-limiting examples of HIA perfume ingredients of Class 2.

TABLE 2

HIA Perfume Ingredients of Class 2

Naphthol(2,1-B)-furan, 3A-Ethyl Dodecahydro-6,6,9A-Trimethyl
Natural Sinensal
Para Hydroxy phenyl Butanone
2-(Cyclododecyl)-propan-1-ol TABLE 2-continued HIA Perfume Ingredients of Class 2

Oxacycloheptadecan-2-one
Ketone,Methyl-2,6,10-Trimethyl-2,5,9-Cyclododecatriene-1-yl
8alpha,12oxido-13,14,15,16-tetranorlabdane
Cyclohexane Propanol 2,2,6 Trimethyl-Alpha,Propyl
6,7-Dihydro-1,1,2,3,3-Pentamethyl-4(5H)-Indanone
8-Cyclohexadecan-1-one
2-(2-(4Methyl-3-cyclohexan-1-yl)-cyclopentanone
Oxacyclohexadecen-2-one
3-Methyl-4(5)-Cyclopentadecenone
3-Methyl-5-(2,2,3-trimethyl-3-cyclopenten-1-yl)-4-penten-2-ol
2,4,-Dimethyl-2-(1,1,44,-tetramethyl)tetralin-6-yl)-1,3-dioxolane
Tridecene-2-nitrile
7,Acetyl,1,2,3,4,5,6,7,8-Octahydro-1,1,6,7-Tetra Methyl Naphthalene
5-Cyclohexadecenone-1

Secondary fragrance compositions of the present invention may also comprise optional conventional perfume composition materials such as other perfume ingredients not falling within either Class 1 or Class 2, odorless solvents or oxidation inhibitors, or mixtures thereof. Secondary fragrance compositions of the present invention may comprise up to 75%, by weight of the composition, of Class 1 and Class 2 HIA perfumes.

Highly Volatile Perfumes

The secondary fragrance of the present invention may be a highly volatile perfume. It is believed that highly volatile perfume materials can provide fragrance aesthetics such as fresh and clean odor impressions.

Nonlimiting examples of highly volatile perfume materials that have a boiling point less than or equal to 250° C. include, but are not limited to, anethole, benzaldehyde, decyl aldehyde, benzyl acetate, benzyl alcohol, benzyl formate, benzyl propionate, iso-bornyl acetate, camphene, cis-citral (neral), citronellal, citronellol, citronellyl acetate, paracymene, decanal, dihydrolinalool, dihydromyrcenol, methyl benzyl carbinyl acetate, dimethyl benzyl carbinyl acetate, dimethyl phenyl carbinol, eucalyptol, helional, geranial, geraniol, geranyl acetate, geranyl nitrile, cis-3-hexenyl acetate, dihydrocitronellal, d-limonene, linalool, linalool oxide, tetra-hydro linalool, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, phenyl acetaldehyde, alpha-pinene, beta-pinene, gamma-terpinene, terpineol, alpha-terpineol, beta-terpineol, terpinyl acetate, vertenex (para-tertiary-butyl cyclohexyl acetate), gamma-methyl ionone, undecalactone, undecylenic aldehyde, alpha-damascone, beta-damascone, amyl acetate, lemon oil, orange oil, and mixtures thereof.

Matrix

Cyclodextrin Complex

The solid antiperspirant compositions of the present invention may include a secondary fragrance that complexes with a cyclodextrin. As used herein, the term "cyclodextrin" includes any of the known cyclodextrins such as unsubstituted cyclodextrins containing from about six to about twelve glucose units, especially alpha-cyclodextrin, beta-cyclodextrin, gamma-cyclodextrin and/or their derivatives and/or mixtures thereof. For example, the present invention may use cyclodextrins selected from the group consisting of beta-cyclodextrin, hydroxypropyl alpha-cyclodextrin, hydroxypropyl beta-cyclodextrin, methylated-alpha-cyclodextrin, methylated-beta-cyclodextrin, and mixtures thereof.

Cyclodextrins and/or mixtures thereof are useful to the present invention since they are particularly known to absorb body odors. Therefore, an added benefit of using cyclodextrins as complexing aids for the secondary fragrance is that once the matrix solubilizes and the fragrance is released, the cyclodextrin may then become available to absorb malodor. Cyclodextrins may be included within the matrix of the present invention from about 0.1%, from about 1%, from about 2%, or from about 3% but no more than about 25%, no more than about 20%, no more than about 15% or no more than about 10%, by weight of the composition.

The release of the secondary fragrance from the complex between cyclodextrin and the secondary fragrance occurs rapidly when wetted with body fluids. This is convenient for use within the present invention since the secondary fragrance should initially remain odorless until aqueous activation and solubilization of the matrix. For example, cyclodextrins having small particle sizes may complex with the secondary fragrance of the present invention and remain odorless within the composition until the body perspires. Particularly, β-Cyclodextrins may be used in the present invention since they have a high tolerance to dissolve in water and will release the fragrance more slowly. Cyclodextrins having a small particle size may aid in providing higher cyclodextrin surface availability for activation. As used herein, the particle size refers to the largest dimension of the particle. Small particle cyclodextrins useful in the present invention may have a particle of less than about 50 microns, less than about 25 microns, or less than about 10 microns. A more complete description of the cyclodextrins, cyclodextrin derivatives and cyclodextrin particle sizes useful in the matrices of the present invention may be found in U.S. Pat. No. 5,429,628, issued to Trinh et al. on Jul. 4, 1995.

Optional Materials

The solid antiperspirant compositions of the present invention may further comprise additional optional materials known for use in antiperspirant, deodorant or other personal care products, including those materials that are known to be suitable for topical application to skin. Non limiting examples include dyes or colorants, emulsifiers, distributing agents, pharmaceuticals or other topical actives, skin conditioning agents or actives, deodorant agents, antimicrobials, preservatives, surfactants, processing aides such as viscosity modifiers and wash-off aids. Examples of such optional materials are described in U.S. Pat. No. 4,049,792 (Elsnau); U.S. Pat. No. 5,019,375 (Ianner et al.) and U.S. Pat. No. 5,429,816 (Hofrichter et al.).

Method of Manufacture

The solid antiperspirant compositions of the present invention may be prepared by any known or otherwise effective technique, suitable for providing an anhydrous composition of the desired form and having the essential materials described herein. Many such techniques are described in the antiperspirant/deodorant formulation arts for the described product forms.

The product of the present invention may be manufactured by limiting the length of time that the secondary fragrance within the water soluble matrix is exposed to heat to prevent deterioration of the inclusion agent. This can be achieved by addition of the secondary fragrance within the water soluble matrix just prior to cooling the antiperspirant composition to room temperature. Another suitable method of manufacture is described in co-pending application filed by Walling et al. on Mar. 1, 2005, entitled "Direct Contact Quench Crystallization Process and Cosmetic Product Produced Thereby".

Method of Use

The solid antiperspirant compositions of the present invention may be applied topically to the underarm or other suitable area of the skin in an amount effective to reduce or inhibit perspiration wetness. Compositions of the present invention may be applied in an amount ranging from at least about 0.1 gram but no more than about 20 grams, no more than about 10 grams, or no more than about 1 gram. The composition may be applied to the underarm at least about one or two times daily, preferably once daily, to achieve effective antiperspirant reduction or inhibition over an extended period.

The solid antiperspirant composition can also be applied every other day, or every third or fourth day, and then optionally to supplement application on off-days with other personal care products such as deodorants and/or conventional antiperspirant formulations.

Compositions of the present invention may be applied to skin, wherein the volatile anhydrous carrier leaves behind a skin-adhering polymer and active-containing film. This film is positioned over the sweat ducts and resists flaking and/or rub-off, thereby being present through multiple perspiration episodes.

EXAMPLES

The following Examples can be made in accordance with the present invention.

An example of a high impact accord is given below in Example 1. An example of an Invisible Solid Antiperspirant is given below in Example 2. The high impact accord in Example 2 is complexed with beta cyclodextrin at 8.50% by weight of the inclusion complex. The High Impact Accord of Example 1 is processed according to co-pending application U.S. 60/682,600 filed by Deckner, et al. on May 19, 2005, entitled "Oil Encapsulation".

Example 1

| HIA Perfume Ingredient name | Conc (% w/w) | ODT (ppb) | Boiling Point (° C.) | ClogP |
|---|---|---|---|---|
| 2-6-nonadienal | 0.5 | ≦50 | 210 | 2.7 |
| Adoxal | 0.5 | ≧50 | 276 | 5.2 |
| Allyl Heptanoate | 5.5 | ≧50 | 212 | 3.4 |
| Beta Gamma Hexenol | 1.0 | ≧50 | 159 | 1.4 |
| Cis 3 Hexenyl Acetate | 2.25 | ≧50 | 179 | 2.3 |
| Citralva Plus | 1.0 | ≦50 | 249 | 3.3 |
| d-limonene | 11.3 | ≧50 | 170 | 4.4 |
| Damarose Alpha | 0.5 | ≦50 | 257 | 3.6 |
| Decyl Aldehyde | 2.25 | ≦50 | 218 | 4.0 |
| Hexyl Cinnamic Aldehyde | 9.0 | ≦50 | 334 | 4.9 |
| Mandarin Aldehyde | 3.5 | ≦50 | 261 | 4.6 |
| ethyl-2-methyl butyrate | 3.5 | ≦50 | 132 | 2.1 |
| Melonal | 1.2 | ≦50 | 188 | 2.6 |
| Methyl Nonyl Acetaldehyde | 1.0 | ≦50 | 237 | 4.9 |
| Natural Sinensal | 3.5 | ≦50 | 295 | 4.5 |
| Nectaryl | 9.0 | ≦50 | 317 | 4.4 |
| Neobutenone | 0.5 | ≦50 | 233 | 3.63 |
| decyl aldehyde | 9.0 | ≦50 | 218 | 4 |
| Para Hydroxy Phenyl Butanone | 1.5 | ≦50 | 301 | 1.1 |
| Pino Acetaldehyde | 3.5 | ≦50 | 257 | 3.3 |
| Trans-2 Hexenal | 0.5 | ≦50 | 145 | 1.6 |
| Undecalactone | 9.0 | ≧50 | 260 | 3.8 |
| methyl-2-nonenoate | 3.5 | ≧50 | 211 | 3.97 |
| Verdox | 11.5 | ≧50 | 237 | 4.1 |
| Ionone Beta | 5.5 | ≧50 | 276 | 3.8 |

The antiperspirants are prepared in the lab using conventional preparation procedures, according to one skilled in the art of making antiperspirants.

| Ingredient | Example 1 | Example 2 | Example 3 | Example 4 |
|---|---|---|---|---|
| | Invisible Solid Antiperspirant Sticks [Conc (% w/w)] | | | |
| Al Zr Trichlorhydrex Glycinate | 20.00 | 20.00 | 25.25 | 24.00 |
| Cyclopentasiloxane | QS | QS | QS | QS |
| Tribehenin (Syncrowax HR-C)[1] | 0.00 | 15.00 | 14.5 | 14.00 |
| C18-36 Acid Triglyceride (Syncrowax HGLC)[2] | 3.75 | 3.75 | 3.75 | 3.75 |
| Petrolatum | 0.5 | 0.5 | 0 | 0 |
| Panthenyl Triacetate | 0.5 | 0 | 0 | 0 |
| Talc | 0 | 0 | 0 | 2.0 |
| Silica | 0 | 0 | 0.5 | 0 |
| C13-C14 Isoparaffin (Isopar M)[3] | 10.00 | 10.00 | 10.00 | 10.00 |
| Dimethicone 50 cs | 5.00 | 5.00 | 5.00 | 5.00 |
| Fully Hydrogenated High Erucic Acid Rapeseed Oil[4] | 15.00 | 0.00 | 0.00 | 0.00 |
| Secondary Fragrance High Impact Accord (from Ex. 1) In Beta Cyclodextrin complex | 0.50 | 2.50 | 3.00 | 1.00 |

[1]Croda, Inc., New York, New York, USA
[2]Croda, Inc., New York, New York, USA
[3]Exxon Chemical Company, Baytown, Texas, USA,
[4]CanAmera, Canada All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the term in a document incorporated herein by reference, the meaning or definition assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. An anhydrous, solid antiperspirant composition comprising:
   a. from about 0.1% to about 30% by weight of an antiperspirant active selected from the group consisting of aluminum halides, aluminum chlorohydrates, aluminum hydroxyhalides, zirconyl oxyhalides, zirconyl hydroxyhalides, and mixtures thereof;
   b. from about 0.1% to about 35% by weight of a thickening agent;
   c. from about 10% to about 60% by weight of an anhydrous liquid carrier;
   d. from about 0.1% to about 5%, by weight of the composition, of a primary fragrance; and
   e. from about 0.1% to about 5%, by weight of the composition, of a secondary fragrance that is distinct from the primary fragrance and is included in a surfactant-free, water-releasable matrix, the secondary fragrance comprises perfume chemicals that are not included in the primary fragrance,
   wherein:
   the surfactant-free, water-releasable matrix is a cyclodextrin complex;
   the anhydrous, solid antiperspirant composition exhibits an Antiperspirant Efficacy Index of at least 0.9; and the anhydrous, solid antiperspirant composition has a product hardness of from 600 gram·force to about 5000 gram·force.

2. The anhydrous, solid antiperspirant composition of claim 1, wherein the anhydrous liquid carrier is free of non-volatile organic liquids having a C log P value greater than 5.5.

3. The anhydrous, solid antiperspirant composition of claim 1, wherein the thickening agent is selected from the group consisting of organic solids, silicone solids, gellants, inorganic particulates, and mixtures thereof.

4. The anhydrous, solid antiperspirant composition of claim 1, wherein the cyclodextrin complex comprises cyclodextrins selected from the group consisting of alpha-cyclodextrin, beta-cyclodextrin, gamma-cyclodextrin, and mixtures thereof.

5. The anhydrous, solid antiperspirant composition of claim 4, wherein the cyclodextrin complex includes a fragrance selected from the group consisting of perfumes, highly volatile perfume materials having a boiling point of less than 250° C., High Impact Accord perfume materials, and mixtures thereof.

6. The anhydrous, solid antiperspirant composition of claim 4, wherein the cyclodextrin complex includes cyclodextrins having a particle of less than 50 microns.

7. The anhydrous, solid antiperspirant composition of claim 4, comprising from about 0.1% to about 25% cyclodextrins, by weight of the composition.

8. The anhydrous, solid antiperspirant composition of claim 1, wherein the composition exhibits a product hardness of from at least 800 gram·force and a residue grade that is less than 35.

9. The anhydrous, solid antiperspirant composition of claim 1, wherein the secondary fragrance comprises one or more Class 2 High Impact Accord (HIA) perfume ingredients, wherein Class 2 HIA ingredients have a boiling point of greater than 275° C. at a normal, standard pressure of about 760 mm Hg.

10. The anhydrous, solid antiperspirant composition of claim 9, wherein the secondary fragrance further comprises one or more Class 1 HIA ingredients, wherein Class 1 HIA ingredients have a boiling point less than 275° C. at a normal, standard pressure of about 760 mm Hg.

11. The anhydrous, solid antiperspirant composition of claim 10, wherein the secondary fragrance comprises from 0.01% to about 75% by weight of Class 1 HIA ingredients and Class 2 HIA ingredients.

12. The anhydrous, solid antiperspirant composition of claim 10, wherein the secondary fragrance comprises from 0.01% to about 25% by weight of Class 2 HIA ingredients.

13. The anhydrous, solid antiperspirant composition of claim 10, wherein the secondary fragrance comprises from about 15% to about 50% by weight of Class 1 HIA ingredients.

14. The anhydrous, solid antiperspirant composition of claim 1, wherein the secondary fragrance comprises no perfume chemicals that are included in the primary fragrance.

15. The anhydrous, solid antiperspirant composition of claim 1, wherein the anhydrous, solid antiperspirant composition is devoid of a malodor reducing agent other than the antiperspirant active.

16. The anhydrous, solid antiperspirant composition of claim 1, further comprising a malodor reducing agent other than the antiperspirant active.

17. The anhydrous, solid antiperspirant composition of claim 16, wherein the anhydrous, solid antiperspirant composition comprises from about 0.05% to about 15% by weight of the composition of the malodor reducing agent other than the antiperspirant active.

18. The anhydrous, solid antiperspirant composition of claim 16, wherein the malodor reducing agent is selected from the group consisting of pantothenic acid, petrolatum, menthyl acetate, uncomplexed cyclodextrins, talc, silica, and mixtures thereof.

\* \* \* \* \*